US00PP15888P2

(12) United States Plant Patent
Cain et al.

(10) Patent No.: US PP15,888 P2
(45) Date of Patent: Jul. 19, 2005

(54) PLUM TREE NAMED 'SUPLUMTWENTYFIVE'

(50) Latin Name: *Prunus salicina*
Varietal Denomination: Suplumtwentyfive

(75) Inventors: David W. Cain, Bakersfield, CA (US); Terry A. Bacon, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 10/867,878

(22) Filed: Jun. 14, 2004

(51) Int. Cl.[7] ..... A01H 5/00

(52) U.S. Cl. ..... Plt./184

(58) Field of Search ..... Plt./184

(56) References Cited

U.S. PATENT DOCUMENTS

PP7,443 P 2/1991 Weinberger et al. ..... Plt./184

*Primary Examiner*—Anne Marie Grunberg
*Assistant Examiner*—June Hwu
(74) *Attorney, Agent, or Firm*—Knobbe, Martens, Olson & Bear, LLP

(57) ABSTRACT

A new and distinct low-chill plum variety, *Prunus salicina* 'Suplumtwentyfive' is disclosed. The new variety has a relatively low winter chilling requirement of 200 hours at or below 7.2° C. The new variety has heavy and regular fruit production in the mild-winter region of California's Coachella Valley where harvest typically begins about 20 days before the 'Red Beaut' (unpatented) harvest begins in California's San Joaquin Valley. 'Suplumtwentyfive' produces large (approximately 55–58 mm diameter), firm, round fruit having smooth black skin and amber-colored flesh. The flavor of the new variety is mildly sweet with mildly-tart skin.

1 Drawing Sheet

Latin name of the genus and species claimed: *Prunus salicina*.
Variety denomination: 'Suplumtwentyfive'.

BACKGROUND OF THE INVENTION

The present invention relates to a new and distinct variety of plum tree, herein after referred to by the cultivar name 'Suplumtwentyfive.' The new variety 'Suplumtwentyfive' originated by hybridization. The variety was hybridized and selected by David Cain. The new variety was first evaluated by David Cain and Terry Bacon in California's Coachella Valley, near Mecca, in Riverside County, Calif.

SUMMARY OF THE INVENTION

The new variety 'Suplumtwentyfive' is characterized by having large (approximately 55–58 mm diameter), firm, and round fruits having a smooth black skin and amber-colored flesh. The flavor of the new variety is mildly sweet (14° brix), and the skin is mildly-tart. The new variety 'Suplumtwentyfive' has a relatively low winter chilling requirement of approximately 200 hours at or below 7.2° C. The new variety possesses heavy and regular fruit production in the mild-winter region of California's Coachella Valley, where harvest begins about May 5, approximately 20 days before 'Red Beaut' (unpatented) harvest begins in California's San Joaquin Valley.

The seed parent of the new variety 'Suplumtwentyfive' is '90P-001' (unpatented) which was selected from a progeny of 'Suplumeighteen' (U.S. Plant Pat No. 7443) crossed with pollen of 'Ambra' (unpatented). The parent varieties were first hybridized in 1996, with the date of planting of February, 1997, and the date of first flowering being February 1999. The pollen parent is an unknown low-chill plum variety. The new plum variety was first asexually propagated by Terry Bacon near Wasco, Kern County, Calif. in 2000, by budding onto 'Flordaguard' (unpatented) rootstock.

The new variety 'Suplumtwentyfive' most nearly resembles its seed parent, '90P-001' in that they both have black skin and amber-colored flesh. It differs from its seed parent by requiring approximately 200 C.U. in order to come out of winter dormancy and crop successfully. In contrast, the seed parent, '90P-001' requires approximately 600 C.U. to bloom and crop successfully. The new variety may also be distinguished from its seed parent in that it does not have bitter skin when ripe, as compared to the bitter skin of '90P-001.' 'Suplumtwentyfive' also differs from the seed parent, '90P-001' in that the fruit of 'Suplumtwentyfive' is more firm than the fruit of the seed parent.

The new plum variety 'Suplumtwentyfive' may be distinguished from presently available cultivars in commerce by the following combination of characteristics: the new variety 'Suplumtwentyfive' most nearly resembles the 'Ambra' (unpatented) plum variety. It may be distinguished from 'Ambra' by requiring approximately 200 C.U. in order to come out of winter dormancy and crop successfully, while 'Ambra' requires approximately 500 winter C.U.

The new variety 'Suplumtwentyfive' has been shown to maintain its distinguishing characteristics through successive asexual propagations by, for example, budding onto 'Flordaguard' rootstock.

BRIEF DESCRIPTION OF THE FIGURE

The accompanying color photographic illustration (FIG. 1) shows typical specimens of the foliage and fruit of the new plum tree variety 'Suplumtwentyfive.' The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED BOTANICAL DESCRIPTION OF THE INVENTION

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England.

The new variety 'Suplumtwentyfive' has not been observed under all possible environmental conditions. The phenotype may vary somewhat with variations in environment such as temperature, daylength, and light intensity, without, however, any variance in genotype.

The descriptive matter which follows pertains to 3 year old 'Suplumtwentyfive' plum trees grown in the vicinity of Wasco, Kern County, Calif., during 2002, and is believed to apply to plants of the variety grown under similar conditions of soil and climate elsewhere.

TREE (measurements taken on two year old tree unless otherwise noted)

General:

*Tree size*.—Medium. Normal for most plum varieties. Reaches a height of approximately 3 meters with normal pruning.

*Tree vigor*.—Vigorous; growth of approximately 1.8 to approximately 2 meters height the first growing season.

*Tree growth*.—Upright-spreading.

*Tree productivity*.—Productive. Fruit set is usually two or more times desired amount for marketable size fruit. Thinning and spacing of fruit is necessary.

*Tree form*.—Vase formed.

*Bearer*.—Regular. No alternate bearing observed.

*Fertility*.—Unknown. Should be planted with another low-chill plum to ensure consistent set.

*Tree canopy density*.—Dense. Pruning is required to open tree vase shape, allowing more sunlight to center of tree.

*Tree hardiness*.—Hardy in all fruit growing areas of California. Winter chilling requirement is approximately 200 hours at or below 7.2° C.

*Tree disease resistance/susceptibility*.—No specific testing for relative plant disease resistance/susceptibility has been designed. Under close observation in Wasco, Kern County, Calif., no particular plant/fruit disease resistance/susceptibility has been observed.

Trunk: (measurements at 30 cm above soil line).

*Trunk diameter*.—Approximately 9 cm. Varies with soil type, fertility, climatic conditions and cultural practices.

*Trunk texture*.—Medium shaggy, increases with age of tree.

*Trunk color*.—Near Greyed-green 198B to Grey 201A. Becomes darker with age.

Branches: (measurements at approximately 90 cm above soil line).

*Branch size*.—Diameter ranged from approximately 4 to approximately 6 cm.

*Branch texture*.—Smooth on 1st year wood, increasing roughness with tree age.

*Branch color*.—Branches vary from near Greyed-green 198C to near Grey-brown 199C.

*Branch lenticels*.—Number: Few — varies from 0 to approximately 5 lenticels per square centimeter. Lenticel number varies widely depending on environmental conditions and vigor of the plant. Color: Near Greyed-green 198C. Length: Approximately 5 mm. Width: Approximately 2 mm.

Flowering shoots: (data taken in July at midpoint of current-season growth).

*Flowering shoot size*.—Average diameter: approximately 5 mm.

*Flowering shoot color*.—Topside: Near Greyed-orange 172A with slight green background; Underside: Near Greyed-orange 172A.

*Flowering shoot lenticels*.—Few — varies from 0 to approximately 20 per linear centimeter. Lenticel number varies widely depending on environmental conditions and vigor of the plant.

*Flowering shoot leaf buds*.—Shape: Ovoid. Width: Approximately 1 mm. Length: Approximately 2 mm. Color: Near Greyed-orange 165A.

*Flowering shoot flower buds*.—Shape: Ovoid. Width: Approximately 2 mm. Length: Approximately 2.5 mm. Color: Near Greyed-orange 165A. Number: Usually 2.

FOLIAGE

Leaves: (data taken in July on fully expanded leaf at midpoint of current-season growth).

*Leaf size*.—Average length: Approximately 85 mm. Average width: Approximately 35 mm.

*Leaf thickness*.—Medium.

*Leaf color*.—Upper surface: Near Green 139A. Lower surface: Near Green 139C.

*Leaf form*.—Obovate.

*Leaf tip*.—Cuspidate.

*Leaf base*.—Cuneate.

*Leaf margin*.—Finely serrated.

*Leaf venation*.—Pinately net veined.

*Leaf surface texture*.—Smooth.

*Leaf petiole*.—Average length: Approximately 10 mm. Average diameter: Approximately 1.5 mm. Color: Near Yellow-green 151B.

*Leaf stipules*.—Number: 2 per leaf bud. Typical length: Approximately 3 to approximately 5 mm.

*Leaf glands*.—Form: Globose but mixed with many randomly-shaped glands. Number: Varies from approximately 4 to approximately 8. Position: Alternate on upper portion of petiole and base of leaf blade. Average size: Approximately 0.5 mm by approximately 0.5 mm. Color: Near Greyed-purple 183A.

FLOWERS (fully opened)

General:

*Flower blooming period, Kern County, Calif.*—First bloom: Approximately Feb. 15, 2002. Full bloom: Approximately Feb. 20, 2002.

*Flower blooming period, Coachella Valley, Calif.* (*low-chill site*).—First bloom: Approximately Feb. 5, 2002. Full bloom: Approximately Feb. 12, 2002.

*Flower diameter*.—Approximately 20 mm.

*Flower aroma*.—Very slight.

Flower peduncle:
*Length*.—Approximately 9 mm.
*Diameter*.—Approximately 0.9 mm.
*Color*.—Near Yellow-green 145B.
Flower petals:
*Number*.—5.
*Arrangement*.—Overlapping.
*Length*.—Approximately 9 mm.
*Diameter*.—Approximately 7 mm.
*Shape*.—Elliptical.
*Apex shape*.—Rounded.
*Base shape*.—Narrows at point of attachment.
*Color*.—White.
*Surface texture*.—Smooth.
*Margins*.—Slightly undulating.
Flower sepals:
*Number*.—5.
*Length*.—Approximately 3 mm.
*Diameter*.—Approximately 3 mm.
*Shape*.—Elliptical with slightly pointed apex.
*Color*.—Near Yellow-green 145A.
*Surface texture*.—Smooth, slightly rippled.
Flower stamens:
*Number*.—Approximately 18 to approximately 24, average approximately 22.
*Average length*.—Approximately 7 mm.
*Filament color*.—White.
*Anther color*.—Near Yellow-orange 19A, with highlights of Orange-red 33B.
*Pollen color*.—Near Yellow-orange 14D just before dehiscence.
Flower pistil:
*Number*.—Usually one, occasionally two.
*Average length*.—Approximately 7 mm.
*Ovary diameter*.—Approximately 0.9 mm.
*Pubescence*.—None.
*Stigma position*.—Stigma extends below anthers.

FRUIT (Data taken at firm-ripe on mature tree managed to obtain maximum quality)

General:
*Fruit harvest Kern County, Calif*.—Date of first pick: Approximately Jun. 5, 2002. Date of last pick: Approximately Jun. 15, 2002.
*Fruit harvest Coachella Valley, Calif.* (*low-chill site*).—Date of first pick: Approximately May 5, 2002. Date of last pick: Approximately May 15, 2002.
Fruit size:
*Length* (*stem end to apex*).—Approximately 50–55 mm.
*Diameter in line with suture plane*.—Approximately 50–55 mm.
*Diameter perpendicular to suture plane*.—Approximately 55–58 mm.
*Average weight*.—Approximately 99 gm.
Fruit form:
*Viewed from apex*.—Rounded, symmetrical.
*Viewed from side, facing suture*.—Rounded, symmetrical.
*Viewed from side, perpendicular to suture*.—Rounded, symmetrical.
Fruit apex shape: Rounded, to slightly flattened.
Fruit stem-end cavity depth: Shallow, approximately 0.9 cm.
Fruit stem:
*Length*.—Approximately 8.8 mm.
*Width*.—Approximately 2 mm.
*Color*.—Near Green 143C.
Fruit skin:
*Thickness*.—Medium.
*Adherence to flesh*.—Tenacious.
*Surface texture*.—Smooth.
*Pubescence*.—None.
*Bloom*.—Moderate amount.
*Color*.—Near Greyed-purple 187A, becoming fully black as fruit ripens.
*Taste*.—Neutral to slightly acidic.
Fruit flesh:
*Ripens*.—Evenly.
*Texture*.—Fine textured, firm, moderately juicy.
*Fibers*.—Few.
*Flavor*.—Neutral to slightly acidic.
*Brix*.—Approximately 14 degrees.
*Juice*.—Moderate amount.
*Aroma*.—Slight.
*Color*.—Amber (near Greyed-yellow 161B).
Fruit use: Dessert. Market, local and long distance.
Fruit shipping/keeping quality: Good. Holds well in cold storage for 6 weeks and maintains good firmness and eating quality. Minimal bruising and scarring in packing and shipping trials.
Stone: (measurements taken on dried stones).
*Stone freeness*.—Clingstone.
*Stone size*.—Length: Approximately 20 mm. Diameter in line with suture plane: Approximately 18 mm. Diameter perpendicular to suture plane: Approximately 8 mm.
*Stone form* (*viewed from side*).—Obovate, coming to a sharp point at the apex.
*Stone form* (*viewed from stem end*).—Somewhat flattened.
*Stone base shape*.—Rounded and retuse at stem attachment.
*Stone apex shape*.—Rounded with a small, sharp point.
*Stone surface*.—Irregularly furrowed throughout. Lightly ridged and pitted throughout.
*Stone sides*.—Equal.
*Stone ridges*.—1 on each side of the suture, small and rounded, beginning at the base and extending throughout the length of the stone.
*Stone outgrowing keel*.—Well developed.
*Stone tendency to split*.—None.
*Stone color*.—Near Greyed-yellow 161B when dried.

What is claimed is:

1. A new and distinct variety of plum tree named 'Suplumtwentyfive' as herein illustrated and described.

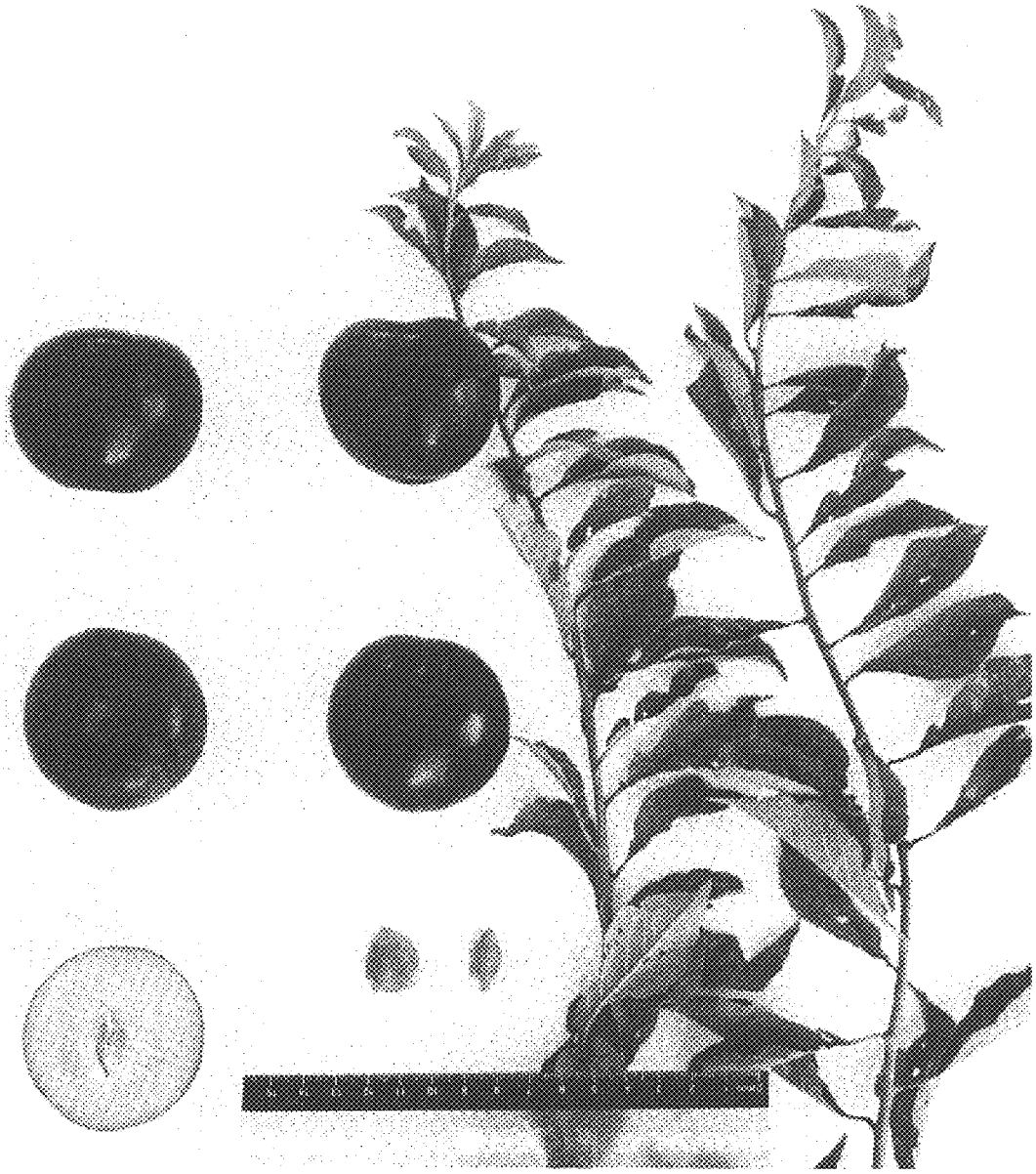

* * * * *